United States Patent [19]

Place

[11] Patent Number: 4,631,060
[45] Date of Patent: Dec. 23, 1986

[54] VAGINAL SPERMICIDE DISTRIBUTING MEMBRANE

[75] Inventor: Virgil A. Place, Half Moon Bay, Calif.

[73] Assignee: Pavex, Inc., San Juan Capistrano, Calif.

[21] Appl. No.: 817,577

[22] Filed: Jan. 10, 1986

Related U.S. Application Data

[60] Continuation of Ser. No. 754,228, Jul. 12, 1985, abandoned, which is a division of Ser. No. 527,850, Aug. 30, 1983, abandoned, which is a continuation-in-part of Ser. No. 441,154, Nov. 12, 1982, abandoned.

[51] Int. Cl.⁴ ............................................. A61F 5/46
[52] U.S. Cl. ..................................... 604/285; 604/55; 128/127
[58] Field of Search ............................ 128/127–131; 604/285, 55, 892

[56] References Cited

U.S. PATENT DOCUMENTS

| | | | |
|---|---|---|---|
| 2,548,775 | 4/1951 | Coel | 128/127 |
| 2,580,133 | 12/1951 | Sheen | 128/127 |
| 2,875,755 | 3/1959 | Heuboski et al. | 128/127 |
| 4,286,593 | 9/1981 | Place et al. | 604/285 |

Primary Examiner—C. Fred Rosenbaum
Assistant Examiner—S. Vinyard
Attorney, Agent, or Firm—Burns, Doane, Swecker & Mathis

[57] ABSTRACT

A vaginal spermicide distributing membrane comprises a relatively thin flexible membrane having a plurality of integral rings of thicker dimension on one or both sides thereof. Each ring can have a depression along its surface that functions as a receptacle for spermicide. The rings provide sufficient resistance to deformation so that when the membrane is flexed for insertion in the vagina, it will tend to assume a planar shape and be held in contact with the vaginal mucosa. The rings keep the device properly positioned and function as successive barriers to sperm migration. Loops provided along the periphery of the membrane assist in its insertion and removal.

20 Claims, 13 Drawing Figures

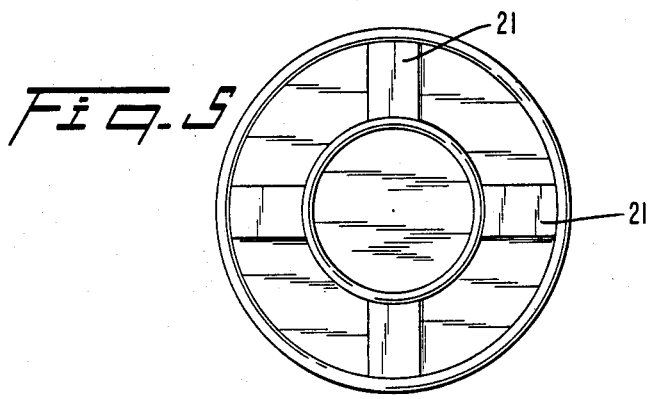
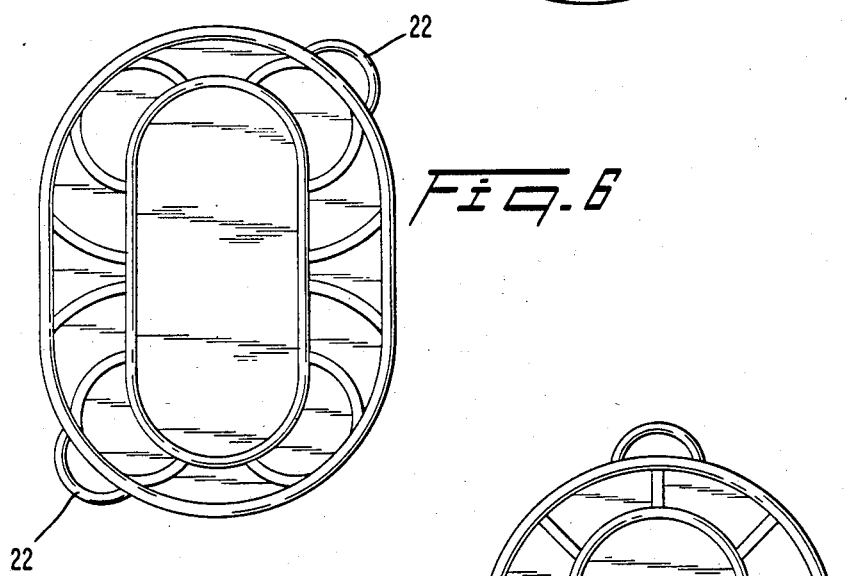
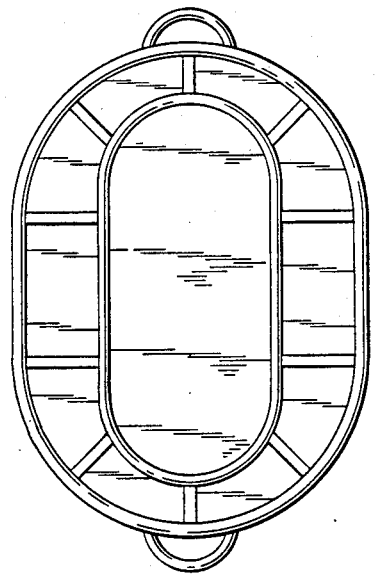

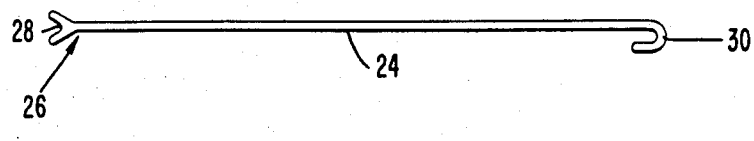
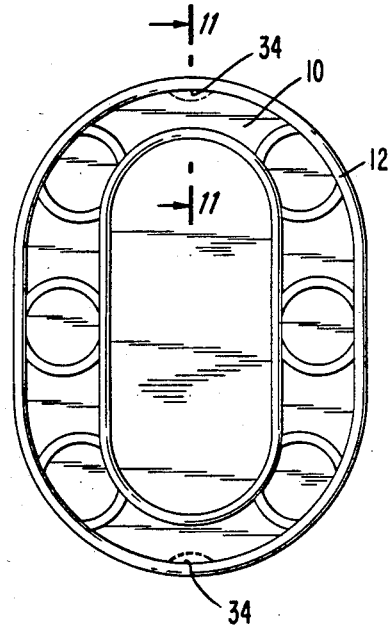
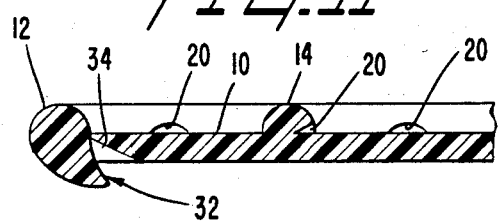
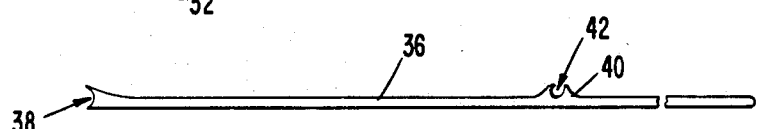
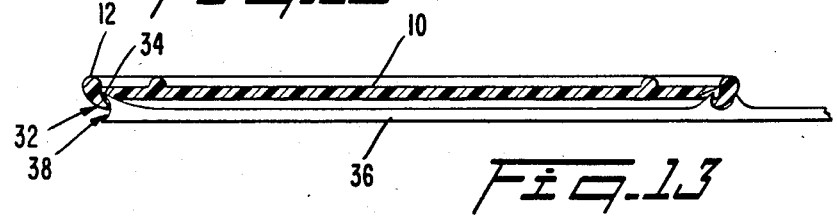

VAGINAL SPERMICIDE DISTRIBUTING MEMBRANE

This is a continuation of application Ser. No. 754,228 dated July 12, 1985, which is a division of Ser. No. 527,850 dated Aug. 30, 1983, which is a continuation-in-part of Ser. No. 441,154 dated Nov. 12, 1982, all of which are now abandoned.

BACKGROUND OF THE INVENTION

The present invention relates to a vaginal contraceptive that is capable of providing both a physical and a chemical barrier to sperm access to the cervix.

One type of contraceptive device that functions to shield the opening to the cervix as well as optimally locate and distribute spermicide within the vagina is disclosed in U.S. Pat. No. 4,286,593. Basically, the shield disclosed in that patent comprises a relatively thick flexible supporting rib structure bonded to a relatively thin flexible film. The rib structure includes a circumferential rib and a series of internal ribs connected to the circumferential rib. The spaces between the various ribs, in combination with the thin film, provide reservoirs for a spermicidal composition. The shield can be bent into a U shape to facilitate insertion into the vaginal cavity, and the rib structure provides sufficient rigidity to cause the shield to return to a generally planar configuration to keep the film and coated spermicide in contact with the vaginal wall.

The shield disclosed in the above-described patent is sound in both structure and function, and it is desirable to improve upon certain aspects thereof. In particular, it is the object of the present invention to provide a novel contraceptive device that incorporates some of the basic principles of that shield but that does not require the bonding of a film to a separate rib structure, and therefore is easier to manufacture. Specifically, it is an object of the invention to provide a novel one-piece conception barrier that can be fabricated using injection molding or compression molding techniques. It is also an object of the invention to provide a conception barrier with improved spermicide receptacles that function as progressive impediments to inactivate sperm. A further object of the invention is the provision of an intra-vaginal conception barrier that can be easily inserted and removed, as well as a device for assisting the insertion and removal thereof.

SUMMARY OF THE INVENTION

In furtherance of these objects, a vaginal spermicide distributing membrane in accordance with the present invention comprises a relatively thin membrane of flexible material having a plurality of integral rings of thicker dimension. The rings are provided on one or both sides of the membrane and can be concentric. In addition, ribs which interconnect the various rings can also be provided to enhance the rigidity of the structure. One or more of the rings and optional ribs can have a groove or a series of wells disposed on an exterior surface to function as additional recepticles for spermicide. The rings provide sufficient resistance to deformation so that when the device is flexed for insertion in the vagina, the potential energy stored therein will cause it to return to a planar shape, maintaining the surface of the shield in close contact with the vaginal mucosa.

The device thus functions as a physical barrier to the cervical opening, as well as a suitable vehicle for the deposit and distribution of spermicide within the vagina. The rings not only function to keep the device properly positioned, but any depressions therein also act as successive impediments to the travel of sperm to the outer periphery of the device and the vaginal walls.

To facilitate insertion and removal of the barrier, it can be provided with one or more loops on its outer periphery to enable an inserter to guide the leading end of the barrier past the cervix to the posterior fornix of the vagina. In a further aspect of the invention, a specific inserter can be affixed to the opposite ends of the barrier to direct it into a position to cover the cervix. Once the barrier is properly positioned, the engagement between the inserter and the barrier can be easily released through a quarter rotation of the inserter to facilitate its removal.

Further features of the invention, and the advantages provided thereby, are explained in detail hereinafter with reference to preferred embodiments of the invention illustrated in the accompanying drawings.

BRIEF DESCRIPTION OF THE DRAWINGS

FIG. 5 is a top view of a further embodiment of the invention;

FIG. 6 is a top view of an embodiment of the invention having loops for ease of insertion and withdrawal of the barrier;

FIG. 7 is a top view of a variation of the embodiment of FIG. 6;

FIGS. 8 and 9 are side view of a device for assisting the insertion and removal of the barrier;

FIG. 10 is a top view of another embodiment of the invention;

FIG. 11 is a partial section side view of FIG. 10 taken along line 11—11;

FIG. 12 is a side view of a second embodiment of the insertion assisting device; and, FIG. 13 is a side view of the device of FIG. 12 in combination with the barrier of FIG. 10.

DETAILED DESCRIPTION

Figure 1:
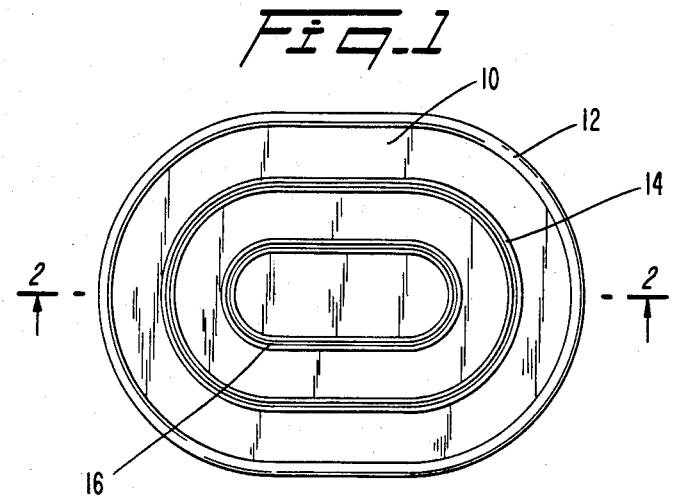
FIG. 1 is a top view of one embodiment of a vaginal spermicide distributing membrane according to the present invention.
Figure 2:
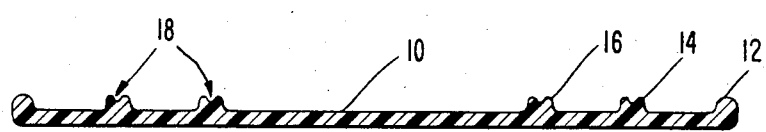
FIG. 2 is a cross-sectional side view of the embodiment of FIG. 1.

Referring to FIGS. 1 and 2 of the drawings, the illustrated embodiment of the invention comprises a flexible membrane 10 with one side thereof having a plurality of elevated integral rings 12, 14 and 16 of greater thickness than the remainder of the membrane. The outermost ring 12 is at the peripheral margin of the membrane and is generally semicircular in cross section, preferably with a smooth, i.e., curved, juncture where it meets the thinner portion of the membrane at its inner edge. The inner rings 14 and 16 are configured similar to the outer ring, except that each is provided with an indentation or depression 18 at its upper surface. These depressions preferably extend around the circumference of each ring, although they can be disposed along only portions thereof, if so desired. They serve as receptacles that retain some of the spermicide coated on the shield, and release it during coitus.

The membrane 10 at its thinnest portion can have a nominal thickness in the range of 0.1–2 mm, for example, to provide sufficient flexibility, depending on the material that is used. Preferably, the membrane is as thin a one as can be reasonably attained while still assuring that a solid layer is formed, i.e., one that can be molded without small holes or other imperfections. Not only does this feature reduce the weight and bulk of the device, but it also results in fragility. In one preferred form, it is desirable that the conception barrier of the present invention be used only once and then disposed, since it typically will be coated with an amount of spermicide that is effective for only one time. Thus, if the membrane is made sufficiently fragile that it will have a tendency to rupture or tear upon removal, there is less probability of re-use.

In contrast to the thinner areas, the rings have sufficient thickness to provide a measure of rigidity to the device. Their thickness can be in the range of 1–10 mm, for example, and preferably is in the range of 4–6 mm. As shown in FIG. 1, the rings are concentric. However, they can also have different arrangements. For example, they can be offset relative to one another, or can comprise a spiral that extends from the margin of the membrane towards its center.

The device can be bowed along its longer axis to facilitate insertion into the vagina. Once inserted, the potential energy against deformation that is stored in the rings causes the device to tend toward maintaining a generally planar configuration. Thus, the periphery of the device will be held in intimate contact with the vaginal walls, assuring a good physical barrier to the cervical os. In addition, the flexibility of the membrane combined with the rigidity of the rings allows the device to adapt to different configurations, thus enabling a single size to comfortably fit most women. By way of example, a conception barrier having an oval configuration such as that shown in FIG. 1 might have a width of 60 mm and a length of 80 mm.

Figure 3:
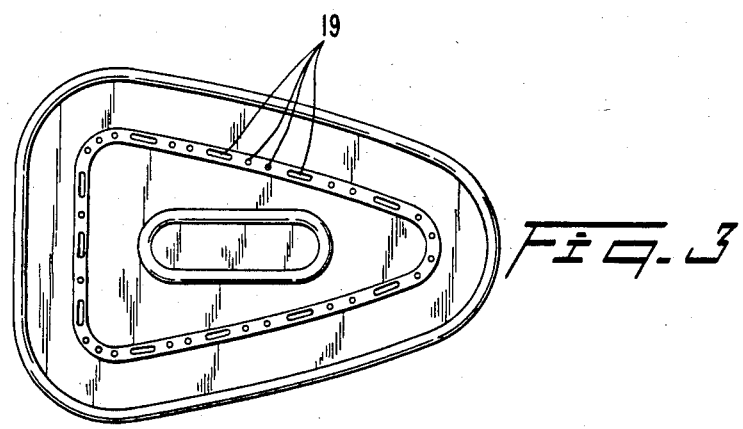
FIG. 3 is a top view of another embodiment of a conception barrier implementing the principles of the present invention.

The depressions 18 have a size that accommodates a suitable amount of spermicide that slowly dissolves during coitus and chemically inhibits migration of the sperm over a prolonged period of time. They can have a semicircular or oblong cross section, with a depth of approximately 0.2–3 mm, for example. As shown in FIGS. 1 and 2, the depressions 18 can be grooves that are provided around the entire circumference of the rings on which they are provided. Alternatively, the depressions can be comprised of a series of wells 19 that are spaced along the surface of the rings, as shown in FIG. 3. These wells can be oval, circular or any other suitable shape, or any combination thereof. The diameter, or cross-sectional width, of the wells can be appropriately chosen to control the duration of the effectiveness of the spermicide. More particularly, as the diameter of a well is decreased, the spermicide that is contained within it will be released (i.e., dissolved) at a slower rate, thus increasing the length of time over which its sperm-killing or inhibiting function is effective.

The grooves or wells that form the spermicide receiving depressions can be located on the sides of the rings as well as on the top margins thereof. In fact, they can be provided by undercutting the rings at their intersection with the planar membrane 10 to provide suitable recesses 20, as best shown in FIG. 11.

Any suitable spermicide can be coated on the membrane, preferably on both sides thereof. Nonoxynol 9, in a gelatinous form, has been found to be one spermicide that functions well in the context of the invention. Other compositions will be apparent to those familiar with this art.

The membrane can be made from a number of materials that are physiologically safe. Preferably, it is made from a thermoplastic material, for example 2–30% ethylene-vinyl acetate, depending on the desired thickness and flexibility. One material that has been found to be particularly suitable in this context is Kraton, distributed by Shell Oil Co. Since the membrane, including the integral thicker portions, is made from one piece of material, it is particularly well-suited to be injection or compression molded.

In the embodiment of FIGS. 1 and 2, the membrane is illustrated as having a generally oblong or oval shape, and rings disposed on only one side thereof. The oval shape is preferred because it provides optimal positioning for the straight, i.e., longer, margins of the device and is most compatible with the long axis of the vagina. However, other shapes can also be utilized. For example, it can be egg-shaped, as shown in FIG. 3. Such a shape may facilitate insertion into the vagina. More particularly, it provides the user with the ability to select whether to insert with the narrow end first (to orient the device as it is being inserted) or with the broad end first (for stabilization within the posterior vagina).

Figure 4:
FIG. 4 is a cross-sectional side view of another embodiment of the invention.

It is feasible to provide rings on both side of the membrane. In such a case, it may be desirable to stagger the rings on opposite sides, as shown in FIG. 4, so as to maintain the overall thinness of the device, as well as assure sufficient flexibility. In addition, the outermost ring 12 is provided with a depression 18 on each side thereof in this embodiment.

If it is found that the membrane tends to compress too easily in the radial direction, such that effective contact with the vaginal walls is not assured, additional thickness can be added at strategic locations, as illustrated in the embodiment of FIG. 5. This additional thickness can be in the form of ribs 21 extending in a generally radial direction between two rings. These ribs can have the same thickness as the rings, but are preferably somewhat less, e.g., 2–4 mm, to maintain minimal thickness. As also shown in FIG. 5, the membrane can have a circular shape.

Additional features can be provided to assist in the insertion and removal of the barrier, as well as enhance its proper positioning. Referring to FIG. 6, a pair of semicircular loops 22 are provided on the external periphery of the outer ring 12. These loops are located adjacent either end of the barrier, slightly offset from its longitudinal axis. Alternatively, as shown in FIG. 7, the loops can be located at the outermost extremes of the barrier, along its longitudinal axis. The loops preferably lie in, or parallel to, the plane of the membrane 10, and can have a thickness equal to or slightly greater than that of the membrane. They need not be as thick as the rings 12, 14, etc., so that they are sufficiently flexible to be easily displaced when the barrier is properly positioned within the vagina.

One of the loops can be used for insertion and the other for removal. Insertion is accomplished by pulling the barrier with the loop located at its leading edge, for example by guiding it with a finger or fingernail. This action is much easier than the pushing that is required when no loops are present. For removal, the finger can be easily hooked onto the other loop and the barrier pulled out.

For social, religious or personal reasons, some women may not desire to use their finger to insert and remove the barrier. In these instances, easy and reliable insertion to the posterior vagina can be achieved with an assistor 24 of the type shown in FIG. 8. One end 26 of the assistor is Y-shaped or otherwise suitably formed to provide a groove or recess 28 which guides one of the loops 22 during insertion. The other end of the assistor can be provided with a hook 30 for grabbing the other loop to remove the barrier.

The assistor 24 can be a unitary structure as depicted in FIG. 8. However, because of its length, it may be preferable that the assistor be jointed as shown in FIG. 9 to enable it to be easily packaged with a barrier. In this case, the assistor is made of two pieces having complementary fittings at their respective ends remote from the recess 28 and hook 30. A hinge 32, for example, a flexible strip, connects these two ends to permit folding of the assistor and yet assure that they remain fitted together during insertion and removal of the barrier.

In the embodiment of FIGS. 6 and 7, the loops are provided on the exterior periphery of the barrier. Alternatively, they can be incorporated within the body of the barrier to eliminate any external projections. Such an embodiment is illustrated in FIGS. 10 and 11. In this embodiment, the outer margin of the barrier is slightly thicker at opposite ends thereof, to provide a discernible lip 32 on the underside of the barrier, as best illustrated in FIG. 11. In the region of this lip, the membrane 10 is undercut to provide a small opening 34. Thus, the loops for inserting and removing the barrier are actually formed by the outer ring 12.

A different embodiment of an assistor can be used to facilitate insertion of the barrier illsutrated in FIGS. 10 and 11. Referring to FIGS. 12 and 13, one end of the assistor 36 is provided with a groove 38, for receiving the lip 32 at one end of the barrier. A raised portion 40 having a recess 42 therein is provided on the assistor at a distance from the end groove 38 that is related to the length of the barrier. Accordingly, this recess is disposed to accomodate the other lip 32 on the opposite end of the barrier, as illustrated in FIG. 13. This assistor can be comprised of two hinged pieces, as in the embodiment of FIG. 9.

When the barrier is engaged on the assistor as shown in FIG. 13, it can be inserted in the vagina and properly positioned to cover the cervix. Once it is so positioned, disengagement of the barrier and the assistor to remove the latter is effected by rotating the assistor a quarter turn, thus releasing the lips 32 from the grooves or recesses.

The barrier can be easily removed from the vagina by grasping or catching one of the lips 32, for example with a fingernail and pulling it.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A process for making a vaginal spermicide distributing contraceptive device providing a physical barrier to the access of sperm to the cervical os and a support for the placement of spermicide when in use, comprising the step of molding a single piece of thermoplastic material into a generally planar flexible membrane having an integral thicker margin at the periphery thereof and at least one integral thicker rings disposed within said thicker margin, said peripheral margin and said ring having sufficient resistance to deformation to provide said membrane with a tendency to resume its planar configuration after being flexed.

2. The process of claim 1 wherein said molding step comprises injection molding.

3. The process of claim 1 wherein said molding step comprises compression molding.

4. A contraceptive device comprising the product of the process of claim 1.

5. The contraceptive product of claim 4 wherein rings are disposed on both sides of said membrane.

6. The contraceptive product of claim 5 wherein the rings on opposite sides of said membrane are alternately staggered relative to one another.

7. The process of claim 1 wherein said membrane has a thickness in the range of 0.1–2 mm at its thinnest areas.

8. The process of claim 1 wherein said ring has a thickness in the range of 4–6 mm.

9. The process of claim 1 wherein at least one of said ring and said peripheral margin is formed with a depression serving as a receptacle for spermicide.

10. A process for making a vaginal spermicide distributing contraceptive device providing a physical barrier to the access of sperm to the cervical os and a support for the placement of spermicide when in use, comprising the step of molding a single piece of thermoplastic material into a generally planar flexible membrane having an integral thicker margin at the periphery thereof, at least one integral thicker ring disposed within said thicker margin, and an integral open loop disposed along said peripheral margin, said peripheral margin and said ring having sufficient resistance to deformation to provide said membrane with a tendency to resume its planar configuration after being flexed.

11. A contraceptive device comprising the product of the process of claim 10.

12. The contraceptive device of claim 11 further including a second loop disposed on said peripheral margin diagonally opposite said one loop.

13. The contraceptive device of claim 12 wherein said loops are located near the longitudinal ends of said device.

14. The contraceptive device of claim 13 wherein said loops are offset from the longitudinal axis of said device.

15. The contraceptive device of claim 13 wherein said loops are located on the longitudinal axis of said device.

16. The contraceptive device of claim 12 wherein said loops project from the external periphery of said margin.

17. The contraceptive device of claim 11 wherein at least one of said peripheral margin and said ring has a depression serving as a receptacle for spermicide.

18. The contraceptive device of claim 17 wherein said depression comprises a groove disposed along the length of circumference of said margin or ring.

19. The contraceptive device of claim 17 wherein said depression comprises a series of wells spaced along the length of said margin or ring.

20. The contraceptive device of claim 19 wherein said wells comprise undercuts at the intersection of said membrane and said margin or ring.

* * * * *